United States Patent [19]

Buttram

[11] Patent Number: 5,383,365
[45] Date of Patent: Jan. 24, 1995

[54] CRACK ORIENTATION DETERMINATION AND DETECTION USING HORIZONTALLY POLARIZED SHEAR WAVES

[75] Inventor: Jonathan D. Buttram, Villamont, Va.

[73] Assignee: The Babcock & Wilcox Company, New Orleans, La.

[21] Appl. No.: 947,123

[22] Filed: Sep. 17, 1992

[51] Int. Cl.$^6$ .......................... G01N 29/04; G01N 9/24
[52] U.S. Cl. ........................................ 73/598; 73/600
[58] Field of Search ................. 73/627, 629, 633, 600, 73/599, 609, 643, 598, 623, 624, 592, 602

[56] References Cited

U.S. PATENT DOCUMENTS

| | | | |
|---|---|---|---|
| 3,955,405 | 5/1976 | Couture | 73/609 |
| 4,226,122 | 10/1980 | Lund et al. | 73/609 |
| 4,269,068 | 5/1981 | Molina | 73/644 |
| 4,274,288 | 6/1981 | Tittman et al. | 73/602 |
| 4,289,030 | 9/1981 | Alers et al. | 73/643 |
| 4,522,064 | 6/1985 | McMillan | 73/592 |
| 4,523,468 | 6/1985 | Derkacs et al. | 73/598 |
| 4,658,649 | 4/1987 | Brook | 73/624 |
| 5,062,300 | 11/1991 | Vallee | 73/623 |
| 5,085,082 | 2/1992 | Cantor et al. | 73/643 |

FOREIGN PATENT DOCUMENTS 61-22834 10/1986 Japan .

OTHER PUBLICATIONS

*UT Operator Training for Planar Flaw Sizing,* EPRI NDE Center, by M. Fuller and S. Walker, Aug., 1984.
Krautkramer, J. & H., "Ultrasonic Testing of Materials," Springer-Verlag, New York Inc., 1969, pp. 7-11, 463.

Primary Examiner—Herbert Goldstein
Assistant Examiner—William L. Oen
Attorney, Agent, or Firm—Daniel S. Kalka; Robert J. Edwards

[57] ABSTRACT

The presence of a crack in a material and the orientation of the crack is determined by placing a transducer on the surface of the material for propagating a shear wave for reflection off of the back wall of the material. The reflected signal is evaluated such that no signal or a weak signal indicates the presence of a crack. The transducer is then held in place and rotated while propagating a shear wave in order to determine the orientation of the crack. The reflected shear wave is then evaluated in the same manner.

8 Claims, 2 Drawing Sheets

CRACK ORIENTATION DETERMINATION AND DETECTION USING HORIZONTALLY POLARIZED SHEAR WAVES

BACKGROUND OF THE INVENTION

1. Field of the Invention

The present invention relates in general to crack detection techniques, and in particular to a new and useful ultrasonic technique for determining crack orientation and detecting cracks using horizontally polarized shear waves.

2. Description of the Related Art

To the knowledge of the applicant no other ultrasonic technique exists that can quantitatively determine the orientation of a crack, that is, the direction of a crack axis of a crack at a given point without moving the ultrasonic transducer from a fixed location.

Commonly used ultrasonic techniques involve the detection of a signal through reflection off of the crack surface. These signals can be weak in amplitude and may be easily missed due to many factors related to both the crack orientation relative to the ultrasonic beam and the bulk material acoustic properties. A common problem found in these techniques is that if no signal is present, the operator may assume the material to be free of cracks, when in fact cracks may indeed exist.

One prior art reference relating to the testing of materials through ultrasound is J. Krautkramer & H. Krautkramer, *Ultrasonic Testing of Materials*, Springer-Verlag (1969) pp. 7-11,463.

U.S. Pat. No. 5,125,272 described an ultrasonic tip diffraction technique for determining the depth of a surface-opening crack. Longitudinal ultrasonic waves are transmitted parallel to and along the crack with measurement of travel time of tip diffracted waves being used to determine the depth of the crack.

SUMMARY OF THE INVENTION

The present invention comprises a method for the ultrasonic inspection of cracks in a component to be examined, in order to either detect and locate the crack or evaluate its physical characteristics. Because any information that can assist in assessing the severity of a crack is considered very valuable, the present invention was designed to provide for crack location as well as information concerning the orientation of the crack.

This method or technique is based upon information obtained from ultrasonic signals. Ultrasound is defined as any sound wave that has a frequency of 20,000 Hz or higher. Transducers are used in order to produce and introduce these sound waves into a material as well as receive it. Conventional ultrasonic transducers contain specially designed piezoelectric crystals that vibrate at the desired frequency when excited by a pulsating voltage field, hence producing ultrasonic sound. These transducers may also operate in a reverse fashion in that ultrasonic vibrations detected by the transducer are converted into electrical signals that can be received by electrical equipment. Electromagnetic acoustic transducers behave similarly, however, an electronic coil and magnet structure are used to induce ultrasonic stress waves instead of a piezoelectric crystal.

The present invention involves propagating horizontally polarized shear waves at an angle perpendicular to the outer surface of a material for crack testing at a point where a transducer is coupled to the material. The technique utilizes commercially available transducers that have piezoelectric crystals cut in the Y-plane or vertical plane as opposed to longitudinal transducers that are cut in the X-plane or horizontal plane. In addition, specially designed electromagnetic acoustic transducers (EMATs) can be used with this technique. These transducers produce ultrasound in a material through electromagnetic forces, do not require physial contact with the material being tested, and can only be used on conducive or magnetic materials. The result of these types of transducers coupled to the surface of a material is that an ultrasonic wavefront propagates normal to the surface with particle displacements in the material parallel to the surface (i.e., horizontal plane). This technique requires that the operator know the direction of particle motion prior to performing a test. This polarization direction is typically indicated by markings on the transducer housing. A standard ultrasonic pulser/receiver and oscilloscope or ultrasonic flaw detector can be used to execute this technique. Special equipment is required for the use of EMATs.

The shear wave technique utilizes back-wall reflection. If the amplitude of this strong reflected signal reduces dramatically as the transducer is moved, then the operator can assume a crack is located at that location.

An object of the present invention is to provide an ultrasonic technique that permits crack detection using a 0° shear wave transducer. This means that only the area directly above the crack, that is the opposite surface of the material, is needed.

Another object of the present invention is to provide an ultrasonic technique that can quantitatively determine crack axis orientation.

Still another object of the present invention is to provide an ultrasonic technique for detecting cracks that does not rely upon energy reflected from the crack surface which can be an unreliable reflector, but rather, the reflection from the opposite surface which is a known, predictable entity, consequently providing a more reliable crack detection technique.

A further object of the present invention is to provide an ultrasonic crack detection technique that is not affected by curved surfaces.

Yet a further object of the present invention is to provide an ultrasonic crack detection technique that uses standard equipment and can easily be used in a field environment.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiments of the invention are illustrated.

DESCRIPTION OF THE PREFERRED EMBODIMENTS

Figure 1:
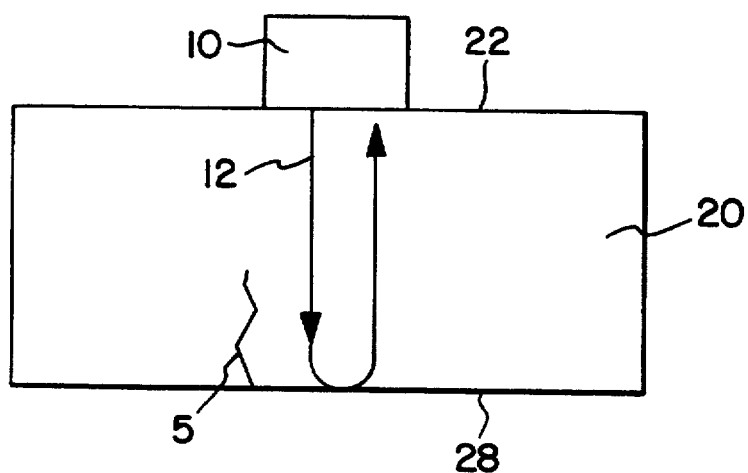
FIG. 1 is a top plan view of a transducer and a block of material for testing according to the present invention.
Figure 2:
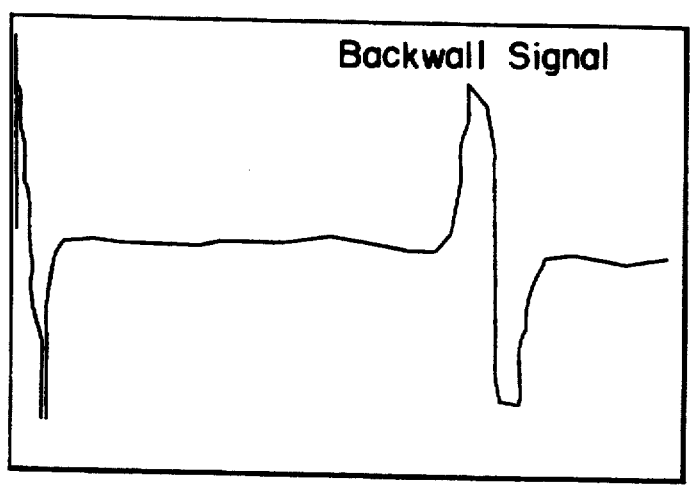
FIG. 2 is a plot of the backwall signal displayed by a CRT according to the present invention.
Figure 3:
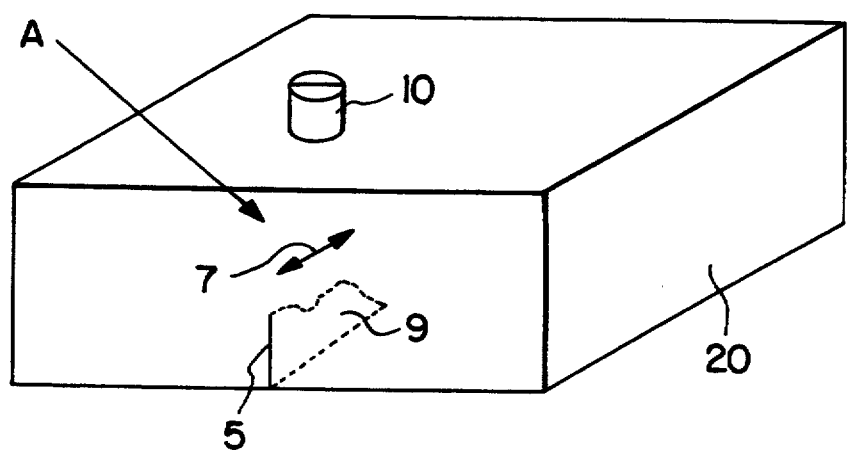
FIG. 3 is a perspective view of a transducer and material showing the direction of particle displacement.

Referring to the drawings, the invention embodied in FIGS. 1 and 3 can both detect a crack 5 and a crack orientation 7, in a material 20, when a horizontally polarized shear wave transducer 10 is placed on the front wall 22 of the material 20, directly opposite of the crack 5. FIG. 1 illustrates this testing arrangement showing the propagating direction of a shear wave path 12. When the transducer 10 is excited with an electrical pulse, ultrasonic energy enters the material 20 along the shear wave path 12. The horizontally polarized shear wave 12 travels through the material 20, from the front wall surface 22 and reflects off the opposite surface or backwall surface 28. This reflected signal 12 returns to the transducer 10 where it is converted to an electrical signal and can be displayed on a CRT or similar signal interpretive device as shown in FIG. 2. FIG. 3 shows that the transducer 10 emits the shear wave 12 in a direction A toward the crack 5 and the crack orientation 7. The arrow A represents the direction of polarization of the transducer (particle displacement direction) is parallel to a crack plane 9, then a backwall signal 12 of normal amplitude will be received. The backwall signal 12 of normal amplitude is also indicative of a location containing no crack. If the polarization direction is perpendicular to the crack plane 9 then the backwall reflection signal amplitude will dramatically decrease or become so small that the signal is no longer detectable indicating the presence of the crack 5. The primary reason for this response is that the shear wave 12 interacts with the crack 5 converting itself into other wave modes which do not return to the transducer 10.

Figure 4:
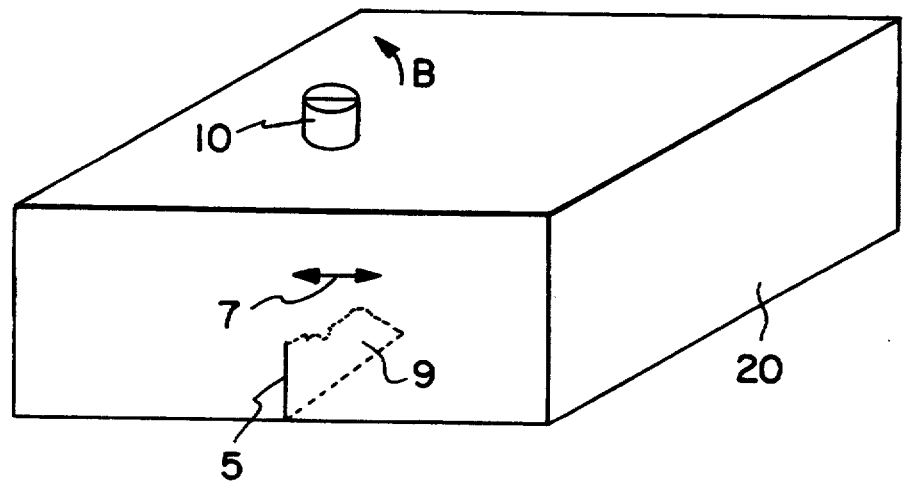
FIG. 4 is a perspective view of a transducer and material showing the transducer rotation direction.

FIG. 4 shows that the orientation 7 of a crack 5 is determined by rotating the transducer 10 in a rotating direction B without introducing any lateral movement along the front wall surface 22 or contact surface. The transducer 10 is rotated until the amplitude of the backwall signal reaches a minimum. The orientation of the crack will be perpendicular or 90° from the polarization direction A indicated in FIG. 3. The transducer should be positioned on the surface opposite from the crack 5 for this technique to be effective.

Information concerning the general orientation of the crack 5 can be of use in the detection and location determination of the crack. If the general orientation of the crack 5 is known (within approximately +1°-45°) then the operator would then scan the area of interest with the polarization direction A normal to the estimated crack plane 9. If the general orientation of the crack 5 is not known, the area of interest should be scanned twice with the polarization direction A of the second scan normal to the polarization direction used in the first scan. Scanning would continue until the amplitude of the backwall signal decreased significantly or until the backwall signal was no longer detected. The location of the transducer 10 that corresponds to this condition is also the location on the surface directly opposite the crack 5.

While the specific embodiments of the invention have been shown and described in detail to illustrate the application of the principles of the invention, it will be understood that the invention may be embodied otherwise without departing from such principles.

What is claimed is:

1. A method for detecting a crack in a material and determining an orientation of the crack, the method comprising the steps of:

placing a transducer at a location on a surface of the material;

propagating a horizontally polarized shear wave from the transducer at an angle perpendicular to an opposite surface of the material;

reflecting the horizontally polarized shear wave off the opposite surface of the material;

receiving the horizontally polarized shear wave reflected off the opposite surface by the transducer;

converting the horizontally polarized shear wave received by the transducer into a first signal having a first strength;

interpreting the first signal for determining the presence of the crack such that the first signal having a weak strength indicates the presence of the crack;

rotating the transducer in a rotating direction about an axis through the location on the surface of the material for determining the orientation of the crack;

propagating the horizontally polarized shear wave in the rotating direction;

reflecting the horizontally polarized shear wave off the opposite surface of the material in the rotating direction;

receiving the horizontally polarized shear wave reflected off of the opposite surface in the rotating direction by the transducer;

converting the horizontally polarized shear wave received by the transducer into a second signal having a second strength; and interpreting the second signal for determining the orientation of the crack such that a second signal having a weak strength indicates the orientation of the crack.

2. A method according to claim 1, wherein the transducer propagates shear waves in a vertical plane.

3. A method according to claim 1, wherein the transducer is activated by an electric pulse in order to propagate the shear wave.

4. A method according to claim 1, wherein the transducer is moved along the surface of the material in order to scan for the presence of the crack.

5. A method according to claim 1, wherein the strength of the first and second signals is determined by evaluating an amplitude of the signals such that the crack is determined when the second signal exhibits a second low amplitude.

6. A method according to claim 1, wherein the signals are interpreted by using a pulser/receiver and oscilloscope.

7. A method according to claim 1, wherein the signals are interpreted by using an ultrasonic flaw detector.

8. A method according to claim 1, wherein the signal is displayed on a crt.

* * * * *